United States Patent [19]    [11] Patent Number: 5,969,243
Frey et al.                                                 [45] Date of Patent: Oct. 19, 1999

[54] HUMIDITY SENSOR FOR CAPACITIVE MEASUREMENT OF HUMIDITY IN BULK MATERIAL

[75] Inventors: Werner Frey, Oggelshausen; German Götz, Dürmentingen, both of Germany

[73] Assignee: Liebherr-Mischtechnik GmbH, Bad Schussenried, Germany

[21] Appl. No.: 08/905,928
[22] Filed: Aug. 5, 1997
[51] Int. Cl.$^6$ .......................... G01R 27/26; G01N 27/12
[52] U.S. Cl. .................. 73/335.04; 73/29.01; 73/74; 324/689
[58] Field of Search ............................. 73/29.01, 335.02, 73/335.03, 335.04, 73, 74; 324/664, 689

[56]         References Cited

U.S. PATENT DOCUMENTS 3,361,944   1/1968   Reinhart .
4,621,228  11/1986   Toki et al. .
5,445,178   8/1995   Feuer .

FOREIGN PATENT DOCUMENTS 0019154  11/1980   European Pat. Off. .
3329025   2/1985   Germany .
748235    4/1956   United Kingdom .

*Primary Examiner*—Daniel S. Larkin
*Attorney, Agent, or Firm*—Dilworth & Barrese

[57]            ABSTRACT

The invention relates to a humidity sensor for capacitive measurement of the humidity contained in a material, predominantly a bulk product. For parallel operation of several humidity sensors, one individual humidity sensor has to fulfil particularly high requirements with regard to accuracy, sensitivity and interchangeability. These requirements are fulfilled by the humidity sensor as per the invention firstly in that at least one pole of a stray field condenser arranged in the humidity sensor is fitted as a conductive layer on the side of a closer plate in the casing of the humidity sensor which is turned away from the material or bulk product. Furthermore, there is arranged in the casing a digital arithmetic-logic unit which exhibits a calibration table stored in a digital memory for determination of humidity levels as a function of measurement signals in a capacity measurement circuit which measures the capacity of the stray field condenser and of interference values affecting the humidity sensor. A further increase in precision, finally, is achieved in that the capacity measurement circuit exhibits an amplitude stabilizer such that the voltage on the stray field condenser is constant over time.

20 Claims, 4 Drawing Sheets

HUMIDITY SENSOR FOR CAPACITIVE MEASUREMENT OF HUMIDITY IN BULK MATERIAL

BACKGROUND OF THE INVENTION

The invention relates to a humidity sensor for capacitive measurement of the humidity contained in a material, predominantly bulk products, also provided with a casing which exhibits a non-conductive closer plate whose outer side is turned towards the material or bulk products or over which material or bulk products travel, and with a stray field condenser arranged in a casing for generation of an electrical stray field whose field lines penetrate the closer plate and the material or bulk products, wherein at least one pole of the stray field condenser is attached as a conductive layer on the side of the closer plate facing away from the material or bulk products.

A humidity sensor of this type is known from patent document DE 36 12 282 and its function is to measure the humidity of a bulk product flowing over a baffle plate which has previously been homogenized as to its density in a reproducible and consistent manner by dropping onto the baffle plate. The correspondingly employed humidity sensor is housed in a plastic casing with a closer plate and mounted on the baffle plate such that the plane of the slip face of the baffle plate is flush with the closer plate. On the side of the closer plate turned away from the bulk product, there is a stray field condenser whose condenser poles are configured by two concentric wire loops. Upon connection of an electrical voltage to the two wire loops, a stray field is formed between the wire loops which penetrates the closer plate and the bulk product flowing over the closer plate. The effect of this is that the bulk product acts in relation to these stray fields as a dielectrical body whose dielectrical constants are largely dependent on the humidity of the bulk product. Since the geometrical condition of the stray field condenser remains constant, it can be assumed that modifications in humidity are approximately proportional to the changes in capacity of the stray field condenser.

These capacity changes are analyzed, in this type of humidity sensor, on the basis tat the stray field condenser is connected with a fixed capacity as a voltage divider, in which context the voltage divider is supplied with power from a high-frequency AC source. Accordingly, a humidity-dependent high frequency voltage is present in the stray field condenser and can be electronically reprocessed. Re-processing is performed by a central analyzer which is connected via a connecting line to the humidity sensor.

It has been found valuable to employ the above-described humidity sensor in particular in the production of transportable concrete, since the concrete quality is also decisively dependent on adherence to the water/cement level and this level can be reliably determined only if the humidity of the additives is taken into account. Particularly high requirements in terms of measurement accuracy and sensitivity of the employed humidity sensors are imposed upon metering of several additives, because the inaccuracies of individual humidity sensors will increment each other. It has been found that in these cases the accuracy and sensitivity of known humidity sensors is not adequate for the production of high-quality transportable concrete. A further problem in parallel operation of several humidity sensors also arises from the fact that the central analyzer is no longer capable of analyzing the data quantities arising. Furthermore, the replacement of an individual humidity sensor in a parallel-operation mixing system is very laborious, because for this purpose the whole mixing function of the system has to be interrupted in order to re-calibrate the individual sensor.

SUMMARY OF THE INVENTION

Accordingly, the purpose of this invention is to produce a humidity sensor of the type described at the outset, which fulfils the requirements in terms of accuracy, sensitivity, interchangeability and data processing for a parallel mixing function.

On the basis of a humidity sensor of this type, one solution under the invention is that at least one pole of the stray field condenser is applied as a conducting layer on the side of the closer plate which is turned away from the material or bulk product. The solution under the invention is based on the fact that due to thinly applied coatings on the reverse side of the closer plate, powerful stray fields can be generated between these coatings perpendicular to the plane of the closer plate. By comparison with a stray field condenser configured from wire loops, this means that a very large number of powerful, useful signals can be generated, which result in higher sensitivity and higher accuracy in the whole sensor.

The closer plate can usefully be made of wear-resistant ceramic plate, preferably consisting of aluminum oxides. The advantage of this is that it is possible to achieve considerable extension of the service life of a humidity sensor in relation to a plastic closer plate, because the additives are commonly highly abrasive materials.

A preferred specification form of the invention is that the conductive layer consists of a metal which is vapor deposited on to the closer plate. This enables the condenser plates to have closer contact with the bulk product, which gives rise to a more favorable dielectrical coating. It has been found in tests that the layer thickness should be between 0.01 and 0.1 mm, and the thickness of the closer plate should be a few millimeters.

In a further embodiment of the invention it is envisaged that the second pole of the stray field condenser should be connected to the potential of the casing or of the baffle plate. For this purpose it is necessary only to envisage one pole as the conductive coating on the closer plate, such that this simplifies its manufacture. Furthermore, the conductive layer acts as a pole point in relation to the potential of the baffle plate and of the casing, because the baffle plate/casing acts as a pole of virtually infinite size. In tests, it has been found that extremely large stray fields can be configured with a circular metal coating whose edge exhibits a distance of a few millimeters in relation to the adjacent baffle plate.

A further advantageous arrangement of the condenser poles may, however, also consist of a solution in which both condenser poles are vapor-deposited onto the closer plate. In this case, the two poles may ideally be arranged in a comb-type or even a strip-type arrangement in relation to each other.

In accordance with a further embodiment of the invention, die casing consists of stainless steel so as to protect the humidity sensor effectively against environmental effects. The casing may usefully consist of a cylindrical extension whose end is blanked off by the closer plate and which is mounted by a flange. The flange may be connected to the baffle plate by screws parallel to the center line of the extension, which can be attached for flush adjustment of the closer plate with the slip face of the baffle plate, using spacers. A particularly simple and effective adjustment of the casing in relation to the baffle plate can also be achieved by using a clamp ring instead of the flange. In such a case, the clamp ring may usefully be equipped with a radial slot and can be clamped by means of a clamp bolt perpendicular to the slot, to mount it on the casing.

A further solution for the above-mentioned objective under the invention, for which patent protection is required, consists of arranging a digital arithmetic-logic unit in the casing, which is equipped for ascertainment of humidity levels as a function of measurement signals from the capacity measurement circuit and determination of disturbance variables acting upon the humidity sensor. The particular advantage of this solution is regarded as being the fact that the humidity sensor can be operated and calibrated independent of a central analyzer. This makes it possible for the humidity sensor to be calibrated even before commissioning and thus be replaced for a defective humidity sensor without laborious calibration activities on site. Furthermore, the digital arithmetic-logic unit can enable data compression in the humidity sensor such that the quantities of data to be transferred to the central analyzer can be considerably reduced.

In order to make it possible to perform basic calibration of the humidity sensor, the calibration table exhibits further input parameters which consist of the disturbance variables acting upon the sensor. In this context, the main disturbance variables are the temperature of the bulk product and the temperature of the capacity measurement circuit which provides a measurement signal as a function of the capacity of die stray field condenser. In a further configuration of the invention, therefore, it is envisaged that the prevailing temperature at the capacity measurement circuit can be measured with an initial temperature sensor, in which context the temperature of the capacity measurement circuit is a further input parameter for the calibration table. It can also be usefully envisaged to have a second temperature sensor which measures the prevailing temperature on the closer plate, whereby the temperature of the closer plate and of the bulk product constitute a further input parameter for the calibration table.

A further disturbance variable to be taken into account arises from density disturbances in the bulk product to be measured, arising due to humidity itself. As an example of this, it is possible to mention the stirring in of a plaster powder, whose volume decreases as soon as it is stirred with water. Density disturbances are material-related and vary hand-in-hand with the nature of the bulk product and material. In order to make it possible to take account of these disturbance effects in a material-related way, it is envisaged that the humidity-related density of the material or of the bulk product should be possible to determine once before the measurement process or during the measurement process as a continuous operation, in which context the humidity-related density of the material or of the bulk product constitutes a further input parameter for the calibration table. It is useful for standard values of common bulk product types to be fed into the computer, such that a predetermined value can be entered as an input parameter for the calibration table according to the quality of the bulk product.

In order to make it possible to apply suitable measurement of the temperature at the capacity measurement circuit, the capacity measurement circuit may usefully be applied on a hybrid switching circuit with an effectively thermally conductive substrate. Aluminum oxide is an example of a useful substrate which has a good temperature conductivity value, which means that a good temperature transfer can be produced between the temperature-related semi conductor components and the first temperature sensor.

A further ideal specification for the invention consists of the computer being connected via a bus line to the central analyzer, in which context the central analyzer of the computer of the humidity sensor issues start commands and calls up the ascertained humidity values. In order to make it possible to minimize line workload, it is usefull to envisage a serial bus line.

In utilization of several humidity sensors, it is useful for the central analyzer to be connected via the bus line with the digital arithmetic-logic units of individual humidity sensors, such that a parallel mixing function is possible with several humidity sensors and low workload for the data to be transmitted and the lines to be laid. As an example, up to 16 humidity sensors can be connected to the bus line.

It is useful for an average of several measurements to be calculated by the digital arithmetic-logic unit located in the humidity sensor, before a humidity value is transferred to the central analyzer. If a humidity sensor is located underneath an additive silo with one coarse outlet and one fine outlet, then it is useful for the corresponding humidity values to be weighted according to the position of the coarse outlet and that of the fine outlet. Since the fine outlet is used only for fine metering after closing of the coarse outlet, it is useful for the measurement values during the fine outlet process to be weighted less than the measurement values during the coarse outlet process. Fine metering can also be performed by having only one outlet flap which is opened fully for coarse metering and only partially open for fine metering. When the system is switched over from coarse metering to fine metering, a fresh averaging process is started, so that at the end of the metering process, two measurement values are passed over from the humidity sensor to the central analyzer. The range of definition for the measurement values can be transmitted to the digital arithmetic-logic unit. By this means, irrelevant values or glitches can be blanked out.

A further solution to the above-mentioned objective under the invention, for which patent protection is required, consists of the capacity measurement circuit exhibiting amplitude stability such that the voltage on the stray field condenser is constant over time.

This solution under the invention takes account of the fact that the conductivity of the material and of the bulk product are included in the measurement as a disturbance variable. In the electrical equivalent circuit, this conductivity value is expressed as an active resistance connected parallel to the stray field condenser. However, if the voltage on the stray field condenser is maintained constant by amplitude stabilization in the capacity measurement circuit, then the conductivity of the material or of the bulk product will exert only a negligible influence. In order to employ amplitude stabilization, recourse may be had, for purposes of a capacity measurement circuit, to an oscillation circuit whose frequency is an index for the stray field condenser capacity. For example, the stray field condenser may be connected in parallel with a coil, in which context the voltage on the oscillation circuit is de-attenuated by an amplifier. In this arrangement, the voltage connected to the oscillation circuit or to the stray field condenser can be held constant by amplitude stabilization, so that changes in the conductivity of the bulk product or of the material exert only negligible repercussions on the resonance frequency of the oscillation circuit.

One further solution to the above-mentioned objective under the invention, for which patent protection is required, consists of a process for calibration of the humidity sensor before its commissioning. In accordance with the process under the invention, a material specimen with known dielectrical characteristics is initially mounted upstream of the closer plate of the humidity sensor. The humidity sensor is alternately cooled down to the lowest permitted operating temperature and heated to the maximum permitted operating temperature. During heat-up, a calibration table is prepared as a function of the measurement signals of the capacity measurement circuit and/or of the first temperature sensor and/or of the second temperature sensor and/or other input parameters, in which context the values are deposited in a permanent memory of the digital arithmetic-logic unit.

The humidity sensor according to the invention is thus consistently calibrated in accordance with a commonly applied process before its commissioning. This makes it possible, in particular, for a humidity sensor to be replaced after its failure or after wear, by an identical type of humidity sensor without the need for re-calibration or re-setting of the whole system. Furthermore, this enables an increase in measurement accuracy since calibration can take place under reproducible laboratory conditions.

An ideal further configuration of the process under the invention consists of the fact that the heat-up process can be controlled as a function of the temperature difference between the first and the second temperature sensors. In particular, heat-up can take place such that the temperature difference between the first and second temperature sensors is always constant. This produces a situation in which the temperature increase within the casing and in particular on the capacity measurement circuit takes place as a linear curve. This in turn produces the advantage that the values for the calibration table can be sampled on the same time basis, since the linear temperature increase means that it is not necessary to take account of inconsistent changes in sampling values.

BRIEF DESCRIPTION OF THE DRAWINGS

Further details and advantages of the invention are explained in greater detail on the basis of a specification example illustrated in the drawings. This drawings illustrate.

DESCRIPTION OF THE PREFERRED EMBODIMENTS

Figure 1:
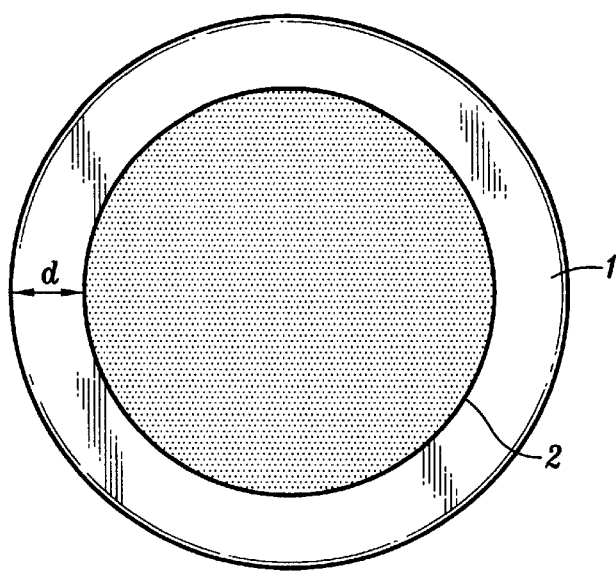
FIG. 1 A plan view of a closer plate with a vapor-deposited metal coating on a humidity sensor, FIG. 2 A perspective view of a humidity sensor with a flange, FIG. 3 A diagram of a baffle plate located underneath an additive silo with a humidity sensor, FIG. 4 A diagram of several humidity sensors arranged in baffle plates, which are connected to a central analyzer by a common bus line, FIG. 5 A flow chart of the arithmetic-logic unit of a humidity sensor, and FIG. 6 A sectional view through a calibration device for a humidity sensor.

FIG. 1 illustrates the plan view of a closer plate 1 of a humidity sensor. Closer plate 1 consists of aluminum oxide ceramics and is specified circular. A metal coating 2 is vapor-deposited concentrically to it on the side turned away from the material or bulk product. In this context, metal coating 2 configures one pole of the condenser whilst the other pole is configured by the surrounding casing or a baffle plate which is located on the plane of the closer plate. It has been found by tests that the thickness of closer plate 1 has to be very much less than the distance d between the outer edge of metal coating 2 and the outer edge of closer plate 1.

Figure 2:
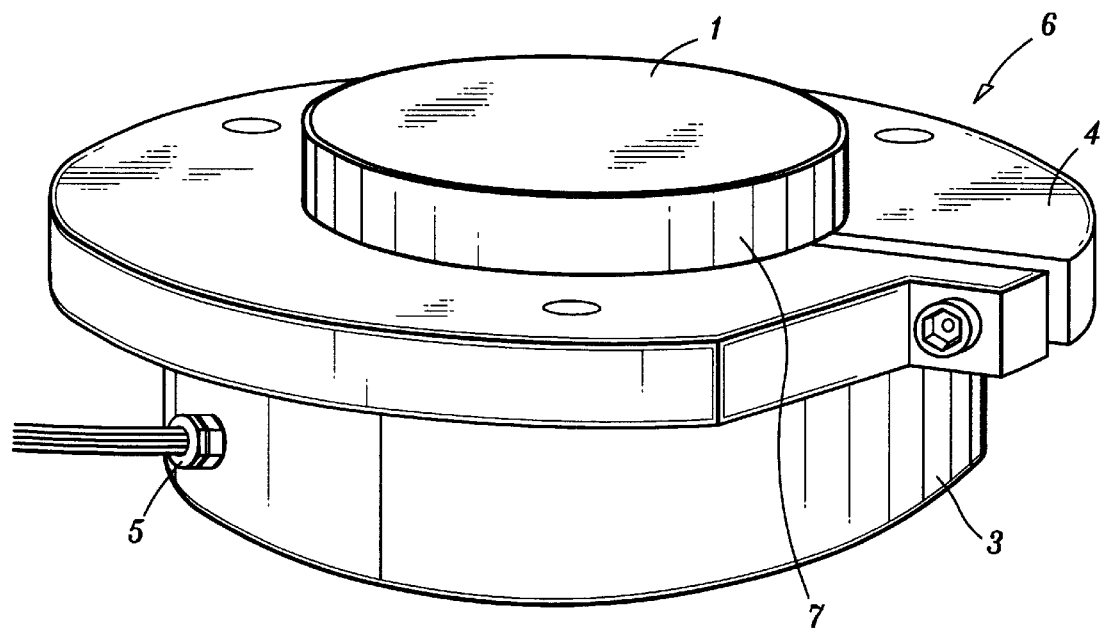

FIG. 2 illustrates a perspective view of a humidity sensor 6. The casing 3 of humidity sensor 6 is held by a flange 4 which can, for example, be bolted in relation to a baffle plate. Above flange 4 there is a cylindrical extension 7, the end of which is closed by the closer plate 1 illustrated in FIG. 1. The side of closer plate 1 which is fitted with metal coating 2 faces into the inside of casing 3. Below the flange there is arranged a cable inlet 5. Casing 3, flange 4 and cylindrical extension 7 are made of stainless steel.

Figure 3:
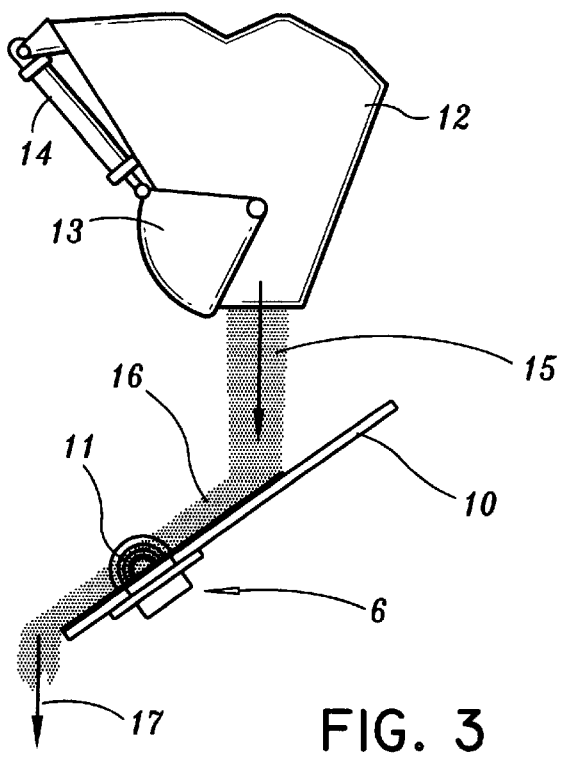

FIG. 3 illustrates the installation of a humidity sensor 6 on a baffle plate 10. Baffle plate 10 is located below the outflow aperture of an additive silo 12. The outflow aperture of the additive silo 12 can be opened and closed by a pivoting flap 13, which can be operated automatically by means of a hydraulic actuator cylinder 14. The bulk product 15 emerging from the aperture of the silo impacts on baffle plate 10 and is deflected by the latter in the direction of humidity sensor 6. The deflection causes the setting up, on baffle plate 10, of a sliding product flow 16 of reproducible density and speed. Humidity sensor 6 is mounted such that the closer plate 1 is fitted in a plane of baffle plate 10 such that the electrical stray field 11 generated by humidity sensor 6 can penetrate the sliding product flow 16. By this arrangement, the volumetric humidity prevailing in the bulk product can be determined. Furthermore, since the material density in sliding product flow 16 is approximately constant, the measured volumetric humidity is proportional to the humidity of the bulk product per unit of weight. The correspondingly determined humidity per unit of weight can now be consulted for calculation of a humidity correction between the additive and water. This correction is performed in a weighing container—which is not described in further detail—into which bulk product 15 is passed in the direction of the arrow 17.

Figure 4:
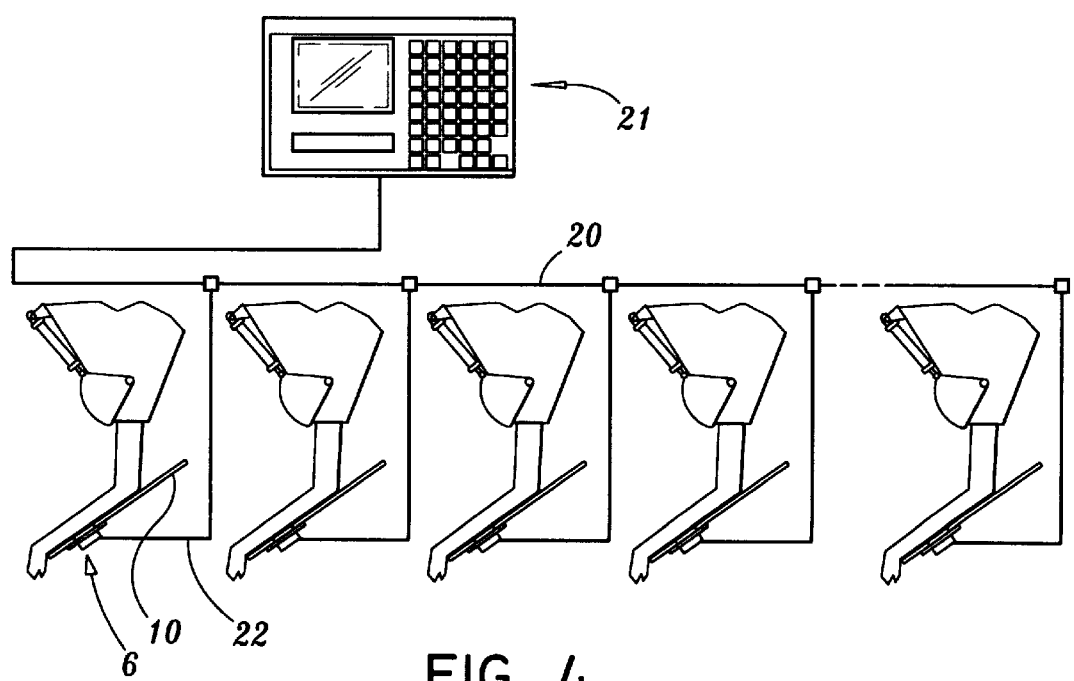

FIG. 4 illustrates a diagram of several humidity sensors 6 which can be operated in parallel and which are arranged in baffle plates 10. The humidity sensors are connected by a common bus line 20 with a central analyzer 21. A connecting cable 22, which is connected to the connector socket 5 of humidity sensor 6, leads from each humidity sensor 6 to bus line 20. In order to keep line workload as low as possible, there is serial data transmission on the bus line. For this purpose, two data lines are required in bus line 20 and in the connecting cable 22, and furthermore the humidity sensor 6 is supplied with power by two additional lines.

For purposes of performing a measurement, the central analyzer 21 transmits a start order to the corresponding humidity sensor 6, to which a corresponding address is allocated. Next, the arithmetic-logic unit arranged in the humidity sensor begins measurement, whereupon several measurement values are averaged over time. Once the measurement is completed, the calculated humidity value is transmitted to the central analyzer 21 as the result. In addition to the humidity level, other data, already processed in the sensor, can also, naturally, be transmitted such as temperatures, average values, fault messages or measurement status. Furthermore the start order from the central analyzer may also contain further information such that measurement can also be performed in parametrized form.

Figure 5:
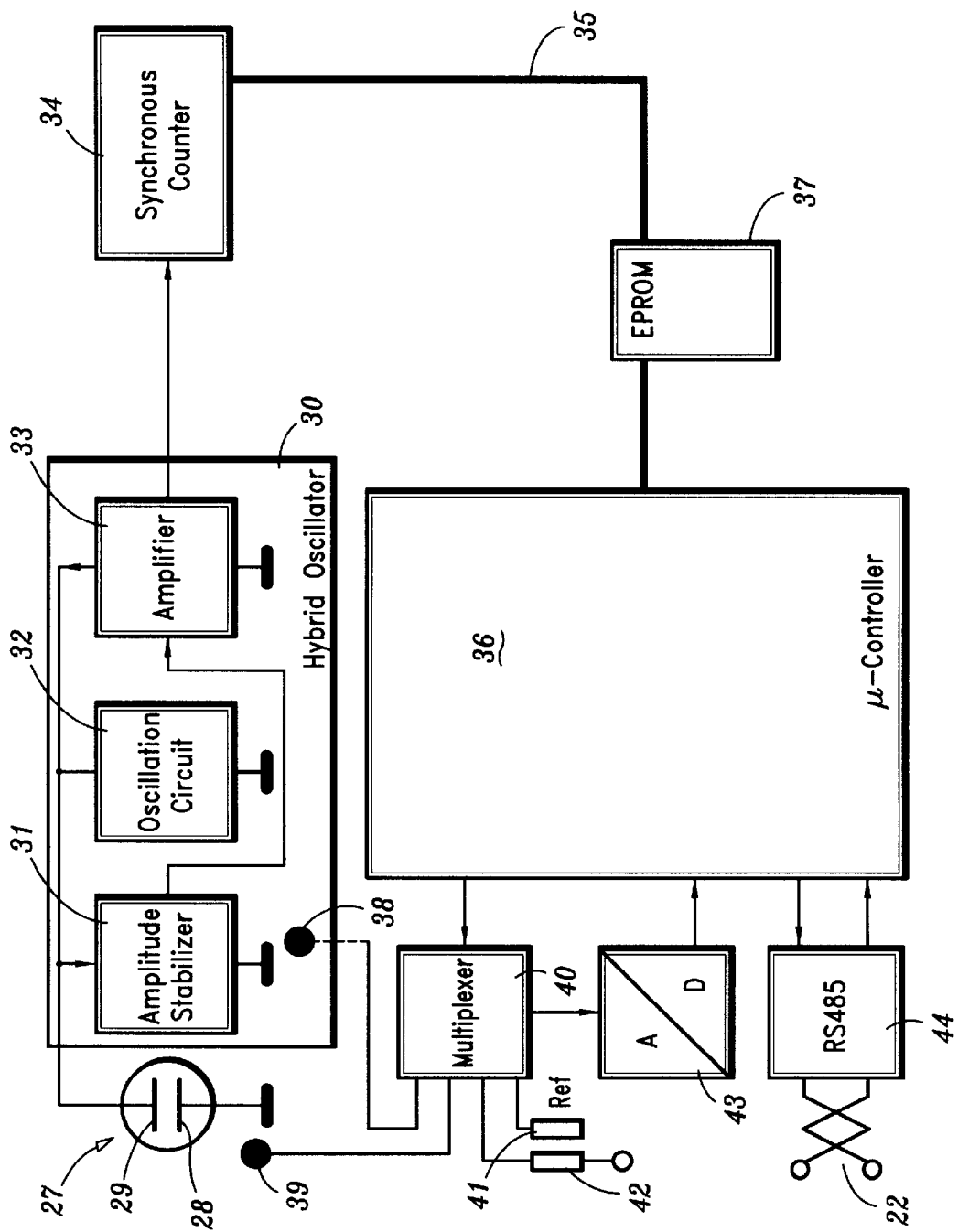

FIG. 5 illustrates a flow chart of the arithmetic-logic unit and the components of a humidity sensor connected to it. Stray field condenser 27 is configured by a pole 28 on the casing side and a pole 29 on the sensor side. The casing-side pole 28 is configured by casing 3 and baffle plate 10 connected to it, and is electrically earthed. In FIG. 5, reference numeral 30 denotes a hybrid oscillator, reference numeral 31 an amplitude stabilizer, reference numeral 32 an oscillation circuit, reference numeral 33 an amplifier, reference numeral 34 a synchronous counter, and reference numeral 40 a multiplexer.

The sensor-side pole 29 is connected with the vapor-deposited metal coat 2. Upon connection of a voltage between poles 28 and 29, a stray field of the stray field condenser 27 is set up, in which context the changes in capacity of stray field condenser 27 are analyzed on the basis of changes in the humidity of the sliding product flow 16, by capacity measurement circuit 30. In parallel with stray field condenser 27, there is connected an oscillation circuit 32 consisting of a coil and one further condenser. Oscillation circuit 32 is de-attenuated by amplifier 33 and oscillates at its resonance frequency in the megahertz range. In this context, amplitude stabilizer 31 maintains a constant voltage at stray field condenser 27. This ensures firstly that amplifier 33 is not over modulated, and also the influence of various conductivities of the bulk product can be effectively suppressed. This is explained by the fact that the conductivity of the bulk product from an electrical viewpoint represents an active resistance parallel to stray field condenser 27, whose variation in resistance is negligible if the voltage on the stray field condenser is maintained constant by amplitude stabilizer 31. The output signal from the amplifier is fed to a synchronous counter 34. For purposes of control of the complete analysis procedure, a microcontroller 36 is envisaged to which several measurement signals can be fed via a multiplexor 40 and an A/D converter 43. Furthermore, microcontroller 36 exhibits an interface to an interface module 44 to which connecting cable 22 can be connected. On bus 35 of the microcontroller, synchronous counter 34 and an EPROM 37 are connected.

The measurement signals of an initial temperature sensor 38, a second temperature sensor 39, a reference voltage source 41 and other measurement signals 42 constitute the input signals of multiplexor 40.

The first temperature sensor 38 measures the temperature on capacity measurement circuit 30, in which context the capacity measurement circuit is made as a hybrid circuit. As a substrate in the hybrid switching circuit, there is employed an aluminum oxide whose effective thermal conductivity ensures reliable temperature measurement for the first temperature sensor 38. The second temperature sensor is connected to closer plate 1 and measures the temperature of the closer plate and of the sliding bulk product on the closer plate. By means of connection 42, further measurement signals, such as the humidity-related density of a bulk product, can be read in via connection 42. Multiplexor 40 is cycled by microcontroller 36 and feeds the corresponding multiplex signal to an AID converter whose digital output value is read in from microcontroller 36.

When microcontroller 36 receives the start command for a measurement order via connecting cable 22 from central analyzer 21, the counter status of synchronous counter 34 is set to zero via bus 35. The cycle signal of amplifier 33 then causes run-up of synchronous counter 34, in which context the count status of synchronous counter 34 indicates the number of resonance oscillations of oscillation circuit 32 over a given period. After a prescribed time which is determined by means of a timer incorporated in microcontroller 36, synchronous counter 34 is read out by microcontroller 36 via bus 35. From the count status and the time elapsed, it is possible to determine the frequency of oscillation circuit 32 which is an index for variations in capacity of stray field condenser 27. Together with the measurement signals read in via multiplexor 40, the calculated frequency then provides the basis of an input parameter for a calibration table which has previously been loaded from the microcontroller out of EPROM 37 in its working memory. The output value for the calibration table is a specific humidity value which can be passed on to central analyzer 21 as a result value from microcontroller 36 via the interface module 44 and connecting cable 22. It may also be possible to perform averaging over several measurement values before measurement values are transmitted to the central analyzer 21.

Figure 6:
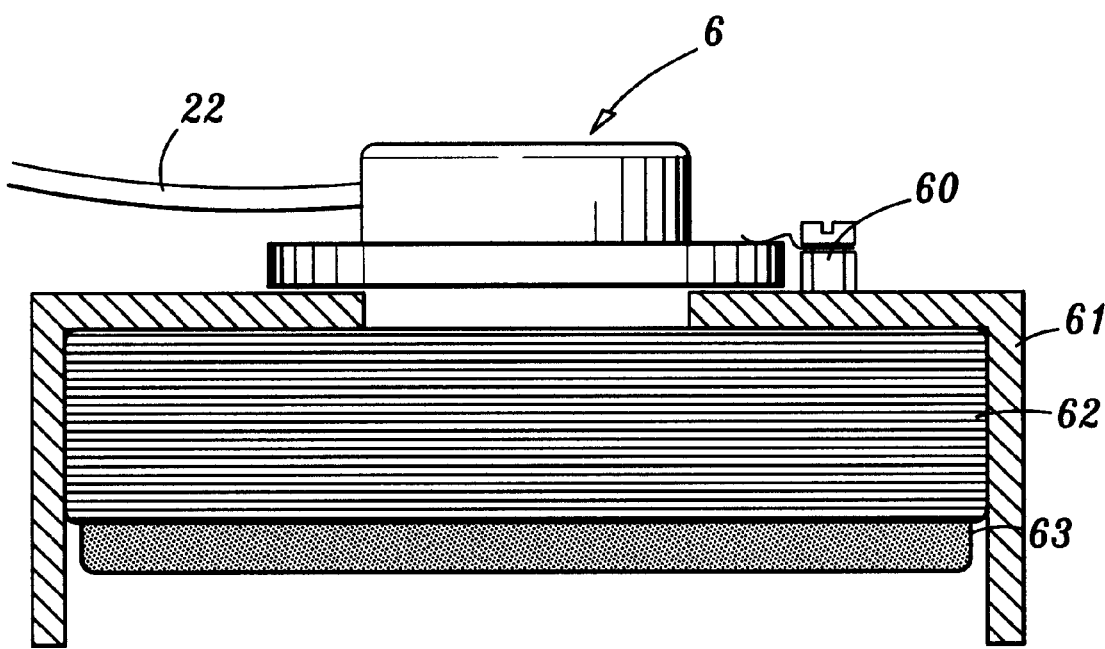

FIG. 6 illustrates a sectional view through a calibration device for a humidity sensor for preparation of a calibration table to be stored in EPROM 37. For this purpose, humidity sensor 6, before its commissioning, is mounted on a metal casing 61 by means of a quick-fitting catch 60. The closer plate 1 of the humidity sensor is on a material specimen of known dielectrical characteristics. The calibration table can be prepared on the basis of the measurement signals reaching multiplexor 40 in the context of the known dielectrical characteristics of the material specimen. For this purpose, the humidity sensor permanently mounted on metal casing 61 is initially cooled down to the lowest permitted operating temperature, i.e. to −10°, for example. This is followed by heating up of humidity sensors to the maximum permitted operating temperature which may, for example, be 80° C. Heat-up takes place by means of a heating plate 63 which is placed underneath material specimen 62. On passing through this temperature range, calibration values for a given humidity at a given frequency of oscillation circuit 32 are stored as a function of the measurement signals of the first temperature sensor 38, the second temperature sensor 39 and further measurement signals. The correspondingly prepared calibration table is stored in EPROM 37 together with the control program of the microcontroller, the contents of the EPROM being loaded into the working memory of the microcontroller when the latter is started.

If heating circuit 63 is continuously operated at maximum output during the heat-up process, then the temperature inside humidity sensor 6 will increase exponentially and will approximate the limit value at a continuously decreasing rate. A temperature rise of this form has the disadvantage that at the beginning of the temperature rise, rapid sensing of the measurement values must take place due to the high degree of change, whilst towards the end of the measurement process, the measurement values vary only slowly and thus an unnecessary number of measurement points is recorded at the sampling rate. For this purpose it may be particularly advantageous to fit the heating circuit with an additional control which ensures that the temperature difference between the first and the second temperature sensor remains constant. Since the first temperature sensor is located inside casing 3 of humidity sensor 6—whilst the second temperature sensor is mounted on the casing itself— the constant temperature difference between both temperature sensors guarantees a constant heat flux from the outside of the casing into the inside. This brings about an approximately constant temperature rise inside the casing, which enables substantially improved pick-up of the calibration values.

We claim:

1. Humidity sensor for capacitive measurement of the humidity contained in a material, predominantly bulk products, comprising a casing which exhibits a non-conductive closer plate whose outer side is turned towards the material or bulk products or over which the material or bulk products travel, and a stray field condenser arranged in the casing for generation of an electrical stray field whose field lines penetrate the closer plate and the material or bulk products, wherein at least one pole of the stray field condenser is attached as a conductive layer on the side of the closer plate facing away from the material or bulk products.

2. Humidity sensor in accordance with claim 1, wherein the closer plate is a wear-resistant ceramic sheet, predominantly consisting of aluminum oxides.

3. Humidity sensor in accordance with claim 1, wherein the conductive layer consists of a metal which is vapor-deposited on the closer plate.

4. Humidity sensor in accordance with claim 1, wherein the second pole of the stray field condenser is connected to a potential of the casing or to the potential of a mounting of the casing in which context the casing or the mounting of the casing are sized such that the pole configured by the conductive layer acts as a pole point.

5. Humidity sensor in accordance with claim 1, wherein both poles of the stray field condenser consist of the conductive layer, in which context the two poles are arranged in relation to each other in a comb and/or strip arrangement.

6. Humidity sensor in accordance with claim 1, wherein the closer plate is fitted on a plane of a baffle plate over which the bulk products flow.

7. Humidity sensor for capacitive measurement of the humidity continued in a material, predominantly bulk products, comprising a casing which exhibits a non-conductive closer plate whose outer side is turned towards the material or bulk products or over which the material or bulk products travel, and
a stray field condenser arranged in the casing for generation of an electrical stray field whose field lines penetrate the closer plate and the material or bulk products, wherein
at least one pole of the stray field condenser is attached as a conductive layer on the side of the closer plate facing away from the material or bulk products, and
the casing consists of stainless steel.

8. Humidity sensor for capacitative measurement of the humidity contained in a material, predominantly bulk products, comprising a casing which exhibits a non-conductive closer plate whose outer side is turned toward the material or bulk products or over which the material or bulk-products travel, and
a stray field condenser arranged in the casing for generation of an electrical stray field whose field lines penetrate the closer plate and the material or bulk products, wherein
at least one pole of the stray field condenser is attached as a conductive layer on the side of the closer plate facing away from the material or bulk products, and
the casing exhibits a cylindrical extension whose end is blanked off by the closer plate and which is held in front of a flange.

9. Humidity sensor in accordance with claim 8, wherein the flange is configured as a clamp ring.

10. Humidity sensor for capacitive measurement of the humidity contained in a material, predominantly bulk products, comprising a casing which exhibits a non-conductive closer plate whose outer side is turned towards the material or bulk products or over which the material or bulk products travel,
a stray field condenser arranged in the casing for generation of an electrical stray field whose field lines penetrate the closer plate and the material or bulk products, and
a capacity measurement circuit which supplies a measurement signal as a function of the capacity of the stray field condenser, wherein
at least one pole of the stray field condenser is attached as a conductive layer on the side of the closer plate facing away from the material or bulk products, and
a digital arithmetic-logic unit is arranged in the casing and exhibits a calibration table stored in a digital memory for determination of humidity values as a function of the measurement signals of the capacity measurement circuit and of disturbance variable acting on the humidity sensor.

11. Humidity sensor in accordance with claim 10, wherein the temperature prevailing on the capacity measurement circuit can be measured by an initial temperature sensor, in which context the temperature of the capacity measurement circuit is a further input parameter of the calibration table.

12. Humidity sensor in accordance with claim 11, wherein the capacity measurement circuit is mounted on a hybrid switching circuit with a highly thermally conductive substrate and that a first temperature sensor measures the temperature of the substrate.

13. Humidity sensor in accordance with claim 10, wherein the temperature prevailing on the closer plate can be measured by a second temperature sensor, in which context the temperature of the closer plate is a further input parameter of the calibration table.

14. Humidity sensor as per claim 10, wherein the humidity-related density of the material or of the bulk product can be continuously determined before or during the measurement process, in which context the humidity-related density of the material or bulk product is a further input parameter of the calibration table.

15. Humidity sensor in accordance with claim 10, wherein the arithmetic-logic unit is connected via a bus line to a central analyzer which issues start commands to the arithmetic-logic unit of the humidity sensor and calls up the ascertained humidity levels.

16. Humidity sensor in accordance with claim 15, wherein the central analyzer is connected via the bus line to the arithmetic-logic units of several humidity sensors.

17. Humidity sensor in accordance with claim 10, wherein the capacity measurement circuit exhibits an amplitude stabilizer such that the voltage at the stray field condenser is constant over time.

18. Humidity sensor in accordance with claim 17, wherein the capacity measurement circuit is an oscillation circuit whose frequency is an index for the capacity of the stray field condenser.

19. Procedure for calibration of the humidity sensor in accordance with claim 10 before its commissioning, comprising the following steps:

a) A material specimen of known dielectrical characteristics is mounted upstream of the closer plate of the humidity sensor, b) The humidity sensor is cooled down to the lowest permissible operating temperature, c) After attainment of the lowest permitted operating temperature, the humidity sensor is heated up to the maximum permitted operating temperature, and d) During heat-up, the calibration table is raised as a function of the measurement signals of the capacity measurement circuit and/or of the first temperature sensor and/or of the second temperature sensor and/or further input parameters and stored in a non-volatile memory of the digital arithmetic-logic unit.

20. Procedure in accordance with claim 19, wherein the heat-up process is controlled as a function of the temperature difference between the first and second temperature sensors.

* * * * *